(12) United States Patent
Behr

(10) Patent No.: US 7,229,285 B2
(45) Date of Patent: Jun. 12, 2007

(54) METHOD AND DEVICE FOR HOLDING AND IDENTIFYING SURGICAL INSTRUMENTS

(75) Inventor: Karl Behr, Herrsching (DE)

(73) Assignee: Gabriele Behr (DE)

( * ) Notice: Subject to any disclaimer, the term of this patent is extended or adjusted under 35 U.S.C. 154(b) by 0 days.

(21) Appl. No.: 10/507,709

(22) PCT Filed: Mar. 13, 2003

(86) PCT No.: PCT/EP03/02640
§ 371 (c)(1),
(2), (4) Date: Mar. 25, 2005

(87) PCT Pub. No.: WO03/075781
PCT Pub. Date: Sep. 18, 2003

(65) Prior Publication Data
US 2005/0153260 A1 Jul. 14, 2005

(30) Foreign Application Priority Data
Mar. 13, 2002 (DE) ................... 102 11 268

(51) Int. Cl.
B65D 83/02 (2006.01)
B65D 85/08 (2006.01)
(52) U.S. Cl. .............. 433/77; 433/27; 206/369
(58) Field of Classification Search ............... 433/27, 433/28, 49, 50, 53, 77, 79, 97; 206/368, 206/369, 495.1, 366, 370, 379, 63.5, 443; 422/300
See application file for complete search history.

(56) References Cited

U.S. PATENT DOCUMENTS

| | | | | | |
|---|---|---|---|---|---|
| 3,583,556 | A | * | 6/1971 | Wagner | 206/373 |
| 4,306,862 | A | * | 12/1981 | Knox | 433/77 |
| 4,660,719 | A | * | 4/1987 | Peterson et al. | 206/379 |
| 4,900,252 | A | * | 2/1990 | Liefke et al. | 433/27 |
| 4,947,984 | A | * | 8/1990 | Kaufman et al. | 206/739 |
| 5,006,066 | A | * | 4/1991 | Rouse | 433/77 |
| 5,172,810 | A | * | 12/1992 | Brewer | 206/369 |
| 5,312,250 | A | * | 5/1994 | Ellman et al. | 433/77 |
| 5,368,164 | A | * | 11/1994 | Bennett et al. | 206/373 |
| 5,525,314 | A | * | 6/1996 | Hurson | 422/300 |
| 5,775,499 | A | * | 7/1998 | Budert | 206/379 |
| 5,967,778 | A | | 10/1999 | Riitano | |
| 6,467,618 | B2 | * | 10/2002 | High et al. | 206/370 |
| 6,636,780 | B1 | * | 10/2003 | Haitin et al. | 700/236 |
| 6,764,306 | B1 | * | 7/2004 | DiMarino et al. | 433/77 |

FOREIGN PATENT DOCUMENTS

DE 32 36 70 8/1920
DE 518 811 2/1931

* cited by examiner

Primary Examiner—Cary E. O'Connor
(74) Attorney, Agent, or Firm—Moore & Van Allen PLLC; Michael G. Johnston

(57) ABSTRACT

A method and device for identification of surgical instruments, in particular of dental instruments, uses a stationary geometric arrangement of instrument holders and a suitable positional allocation of the instruments to these holders. The holders are provided in an arrangement of raster modules which cooperate with a base unit, only a single raster module being accessible in each case for removal and fitting of instruments.

14 Claims, 2 Drawing Sheets

METHOD AND DEVICE FOR HOLDING AND IDENTIFYING SURGICAL INSTRUMENTS

The invention relates to a method for identification of surgical instruments, in particular of dental instruments, such as scalpels, drills, files, etc., in each case before and after use, and to a device for carrying out such a method.

In the field of dentistry in particular, frequently used instruments, for example drills, have to be able to be identified and automatically recognized by type. This identification is becoming increasingly important particularly in modern dentistry, because the use of instruments such as drills is increasingly being done by intelligent control appliances which, depending on the type of drill used, automatically control the speed of rotation, torque and parameter characteristics. The required identification has hitherto been done by manual input or selection of the actual drill type via a keyboard, by the dentist, but this is awkward, time-consuming and associated with high risks of error.

To identify surgical and dental instruments, one possibility is to use an optical coding by bar code, etc. This optical coding is, however, problematic in the case of small instruments, such as drills, because of the small dimensions and, in addition to this, is not practicable because of the risk of contamination. It is also conceivable to perform identification by means of a magnetic coding, but this would have to be performed in advance by the instrument manufacturer and is difficult to implement on the market, especially since the coding remains limited to a subquantity of the instruments, and magnetic coding only permits a small code range, which leads to ambiguities in the identification. A magnetic coding is therefore not practicable.

A further possibility for providing identification is to use an electronic coding with a transponder, but this cannot be done because of the required temperature exposure during sterilization of instruments after use.

In addition to the specific individual identification of surgical instruments, in particular of dental instruments, for their specific control, there is also a need for monitoring and recording the duration of use and intensity of use of individual instruments and for suitable improvement in sterilization logistics for the instruments.

Accordingly, the object of the invention is to make available a method and a device of the generic type mentioned at the outset, which can be realized without technical problems and which permits a reliable and producible identification.

With the method according to the invention, a reliable identification of individual instruments is permitted in a simple manner on the basis of a first position in a predetermined desired arrangement, which position can be clearly assigned or prearranged. According to the method, a stationary geometric arrangement of holders for the instruments is first provided, which arrangement in each case has a first holder for insertion of a sterilized instrument and a second holder for insertion of the same instrument after use.

This is followed by positional allocation of instruments to the respective instrument holders in the arrangement; the duration of use of individual instruments is preferably determined by means of the removal and return procedures of the individual instruments being detected and recorded, and the position detection data for control and monitoring are individually evaluated and stored. It is further preferred that at least the treatment section of each used instrument is cleaned in the second holder, for example by a sterilization liquid.

In terms of the device, the invention is characterized by an arrangement of raster modules which each have two instrument holders, and by a base unit which has a section for the respective raster module holder, which is accessible only for removal and fitting of the respective raster module.

Each raster module is preferably accessible by opening a closure lid assigned to the raster module holder. Alternatively, each raster module is accessible by being partially withdrawn from the raster module arrangement, in which case each raster module can preferably be moved out of the raster module arrangement on an associated carriage.

According to a further alternative, each raster module is accessible by being partially pivoted out from the raster module arrangement, in which case each raster module can preferably be arranged on an associated pivot part of the base unit.

The raster modules can be arranged exchangeably on the raster module sections and can be secured detachably by means of, for example, a detachable locking arrangement or in some other way.

According to a preferred further embodiment of the invention, the accessible state of each raster module can be detected by means of a sensor, and the detection signal can be transmitted to an evaluation unit. In this way, it is possible not only to identify and retrieve the relevant instrument automatically, but also to monitor and record the duration of use and intensity of use of individual instruments. In this connection, it is also advantageous if the evaluation unit for monitoring the duration of use of the individual instruments is connected to a processor, a memory and a display.

According to a preferred embodiment of the invention, the base unit comprises the evaluation unit and other electronic components, by which means the raster modules can advantageously be easily sterilized without electronic devices after removal from the base unit.

According to a further embodiment of the invention, it is expedient, for retrieving a specified instrument, if the base unit for each raster module has a preferably optical signal transmitter for the operational state of the associated instrument.

The base unit preferably has a means by which, upon access to one raster module, the other raster modules are maintained inaccessible. This means can be realized for example in the form of a mechanical lock. Alternatively, electronic means can also be provided, it being ensured that only one sensor or switch is in the ON state at any one time. In this way, it is possible to effectively avoid operational errors caused by multiple removal from the magazine-like raster modules arranged next to one another.

According to a further embodiment of the invention, raster modules are combined as a magazine unit, each magazine unit having a coding that can be detected by the base unit. In this way, in combination with automatic detection, different raster module arrangements can be suitably combined with the same base unit.

To improve the sterilization conditions for the instruments, a further embodiment provides that each raster module has a container which is assigned to the holder for a used instrument and which contains sterilization liquid into which the used instrument can be partially immersed.

According to the invention, for identification of the individual instruments on the basis of the fixed position provided in the defined geometric arrangement of raster modules, either an opening mechanism or a slide mechanism or a tilting mechanism is provided, this being assigned to the raster module holder of the base unit. The desired raster module position is in each case determined and coded either by opening of a lid, by moving a carriage out or by tilting the raster module forwards, by a sensor or by a switch group and electronically transmitted to a corresponding separate evaluation unit, for example an Endostepper, by radio, by infrared or by cable, if the evaluation unit is not arranged in the base unit. For the added object of monitoring the duration of use of the individual instruments, suitable logistics consisting of processor, memory and display can also be provided, this object also being able to be achieved by a separate device according to the invention.

The basic design of the device according to the invention has in principle two main structural groups, on the one hand the base unit and on the other hand the arrangement of raster modules which are designed in the manner of a magazine and can be fitted on the base unit. The necessary electronic components are arranged in the base unit, while the raster module arrangement or the magazine represent the components for the geometric/mechanical arrangement. This separation is expedient in view of the required sterilization of the holder for the instruments, since the raster modules are designed without electronics and the base unit provided with electronics remains protected from the high sterilization temperatures. The magazine for the combination of several raster modules has the added advantage that several magazines can in each case be used in conjunction with one base unit, in which case the magazines can be differentiated by a suitable coding.

In each raster module there are two holders for each instrument type, one holder for a sterile or fresh instrument, and the other holder for the already used instrument, in which case the used instrument holder is assigned a receptacle containing a standard sterilization liquid, for example NaOCl, in order to clean the used instrument at least partially by immersion.

An illustrative embodiment of the invention is explained in more detail below with reference to the attached drawings, in which.

Figure 1:
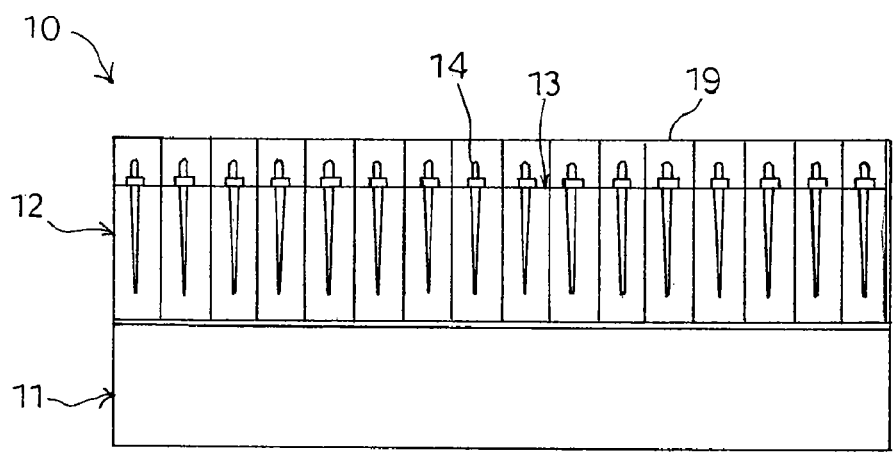
FIG. 1 shows a front view of a device according to the invention.
Figure 2:
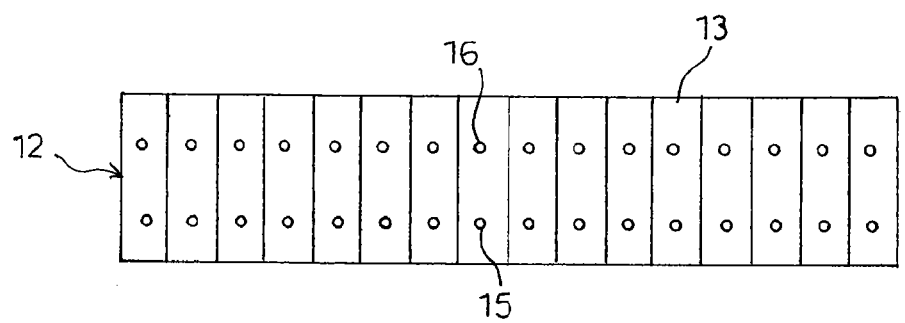
FIG. 2 shows a top view of a magazine-like arrangement of raster modules.

FIG. 1 is a diagrammatic front view of an illustrative embodiment of a device 10 according to the invention for identification of surgical instruments, in particular of dental instruments. The device 10 consists of a base unit 11 and of a magazine-like arrangement 12 of individual raster modules 13 in which, in this illustrative embodiment, dental instruments in the form of drills 14 are arranged.

Each raster module 13 is made of a transparent material and has a holder 15 for sterilized drills and a holder 16 for used drills. Because of the magazine-like, tiered arrangement of the raster modules 13, the holders 15 and 16 are each arranged in a line.

Figure 3:
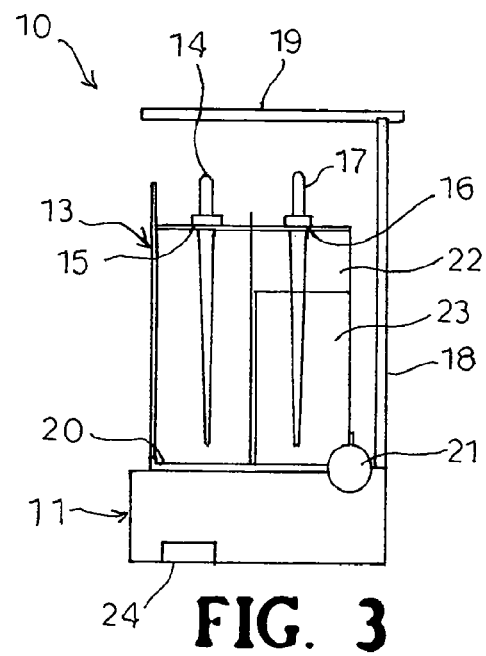
FIG. 3 shows an enlarged diagrammatic side view of the device shown in FIG. 1.

FIG. 3 is a diagrammatic enlarged side view of the device 10. The base unit 11 includes a vertical rear wall 18 and a cover 19, which can each be made of transparent material. Reference number 20 designates a raster module section which, in the area of the vertical rear wall 18, has a tilt axle 21 extending parallel to the rear wall 18. The raster module holder 20 serves only to receive a single raster module 13, which is secured on it, for example by locking in the bottom area.

The figure also shows a used drill 17 which is arranged in the holder 16 of the raster module 13 and whose lower half protrudes into a container 22 which is filled to over three quarters with a sterilization liquid 23.

Figure 4:
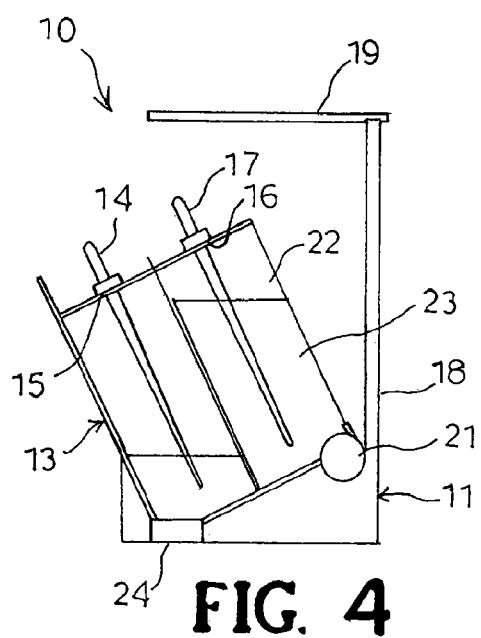
FIG. 4 shows the view of the device according to FIG. 3, with a raster module pivoted out.

In the state shown in FIG. 3, the holders 15, 16 and the drills 14, 17, respectively, are not accessible. If a raster module 13 is pivoted out from the arrangement via the tilt axle 21, as is shown in FIG. 4, access to the instruments 14 and 17 is obtained. FIGS. 3 and 4 also show a touch switch 24 which reports the pivoted-out state of a raster module 13 to electronics (not shown) in the interior of the base unit 11, which sends a signal to a separate evaluation unit (not shown), for example an Endostepper, by radio, by infrared or by cable. A mechanical or electronic means can also be provided (in a manner not shown) to ensure that, after tilting of the raster module 13, another raster module 13 cannot also be tilted outwards. In a manner not shown here, the base unit also has, for each instrument holder 15, 16, an electrical sensor which reports the respective operational state of the associated instrument holder.

The invention claimed is:

1. A device comprising an arrangement of raster modules, each raster module including at least two instrument holders for holding surgical instruments; a base unit including raster module holders for holding the raster modules, and means for accessing the raster modules, wherein only one raster module is selectively accessible for removal and fitting of instruments.

2. The device according to claim 1, wherein the accessing means comprises a closure lid, and wherein each raster module is accessible by opening the closure lid operatively associated with the raster module holder.

3. The device according to claim 1, wherein the accessing means comprises each raster module being accessible by partial withdrawal from the raster module arrangement.

4. The device according to claim 3, wherein each raster module is movable out of the raster module arrangement on an associated carriage.

5. The device according to claim 1, wherein the accessing means comprises a pivoting connection between the raster module arrangement and the base unit, and wherein each raster module is accessible by being partially pivoted out from the raster module arrangement.

6. The device according to claim 5, wherein each raster module can be arranged on an associated pivot part of the base unit.

7. The device according to skim claim 1, wherein the base unit comprises a sensor or switch, and an evaluation unit, and wherein the accessible state of each raster module is detectable by means of a the sensor or switch and the detection signal is transmittable from the sensor or switch to the evaluation unit.

8. The device according to claim 7, wherein, the base unit further comprises a processor including a memory and a display, the processor operatively connected to the evaluation unit for monitoring the duration of use of individual instruments.

9. The device according claim 1, wherein the base unit comprises an evaluation unit.

10. The device according to claim 1, wherein the base unit comprises a signal transmitter for each raster module, the signal transmitter for signalling the state of instruments located in the holders.

11. The device according to skim claim 1, wherein the base unit comprises means for preventing access to the other raster modules upon access to one raster module.

12. The device according to claim 1, wherein several raster modules are designed as a magazine unit which has a coding that can be detected by the base unit.

13. The device according to claim 1, wherein the base unit comprises an optical signal means for each raster module.

14. The device according to claim 1, wherein each raster module comprises a container which is allocated to one of the instrument holders for holding a used instrument, and a sterilization liquid disposed in the container and into which the used instrument can be partially immersed.

\* \* \* \* \*

UNITED STATES PATENT AND TRADEMARK OFFICE
CERTIFICATE OF CORRECTION

PATENT NO. : 7,229,285 B2  Page 1 of 1
APPLICATION NO. : 10/507709
DATED : June 12, 2007
INVENTOR(S) : Karl Behr It is certified that error appears in the above-identified patent and that said Letters Patent is hereby corrected as shown below:

Column 4, line 50, delete "skim"
Column 4, line 53, delete"a"

Signed and Sealed this

Twenty-first Day of August, 2007

JON W. DUDAS
*Director of the United States Patent and Trademark Office*